United States Patent [19]
Tanaka et al.

[11] Patent Number: 6,166,068
[45] Date of Patent: Dec. 26, 2000

[54] IMMUNOMODULATOR, CELL ADHESION INHIBITOR, AND AGENT FOR TREATING, AND PREVENTING AUTOIMMUNE DISEASES

[75] Inventors: Keiichi Tanaka, Toyama; Shinji Makino, Kurobe; Ichiro Oshio, Toyama; Tomoya Shimotori, Toyama; Yukihiko Aikawa, Toyama; Takihiro Inaba, Namerikawa; Chosaku Yoshida, Takaoka; Shuntaro Takano, Mitaka; Yoichi Taniguchi, Takaoka, all of Japan

[73] Assignee: Toyama Chemical Co., Ltd., Tokyo, Japan

[21] Appl. No.: 09/346,932

[22] Filed: Jul. 2, 1999

Related U.S. Application Data

[63] Continuation of application No. 08/530,177, May 6, 1996, Pat. No. 5,922,755, and a continuation of application No. PCT/JP94/00585, Apr. 7, 1994.

[30] Foreign Application Priority Data

Apr. 9, 1993 [JP] Japan ................................ 5-107464

[51] Int. Cl.$^7$ .......................... A61K 31/35; A61K 31/38; A61K 31/40
[52] U.S. Cl. .......................... 514/460; 514/456; 514/451; 514/444; 514/422
[58] Field of Search .................... 514/460, 456, 514/444, 422, 451

[56] References Cited

U.S. PATENT DOCUMENTS 4,954,518  9/1990  Takano et al. .................... 514/456

FOREIGN PATENT DOCUMENTS 38 34 204  4/1989  Germany.

OTHER PUBLICATIONS

Keiichi Tanaka et al, "Pharmacological Studies on 3–Formylamino–7–methylsulfonylamino–6–phenoxy–4H–1–benzopyran–4–one (T–614), a Novel Antiinflammatory Agent. 4$^{th}$ Communication: Inhibitory Effect on the Production of Interleukin–1 and Interleukin–6", *J. Pharmacobio-Dyn.*, 15, pp. 649–655, 1992, XP 000647613.

K. Tanaka et al, "Pharmacological Studies in T–614, A Novel Antiinflammatory Agent: Effect on Type II Collagen–Induced Arthritis in DBA/1J Mice and Spontaneous Arthritis in MRL/1 Mice", *Int. J. Immunotherapy*, X(2), pp. 69–78, 1993, XP 000647615.

K. Tanaka et al, "Pharmacological Studies of the New Antiinflammatory Agent 3–Formylamino–7–methylsulfonylamino–6–phenoxy–4H–1–benzopyran–4–one", *Arzneim.–Forsch./Drug Res.*, 42(1), 935, 1992, XP 000647665.

K. Tanaka et al, "Pharmacological Studies of the New Antiinflammatory Agent 3–Formylamino–7–methylsulfonylamino–6–phenoxy–4H–1–benzopyran–4–one", *Arzneim.–Forsch/Drug Res.*, 42(11), Nr. 7, 1992, XP 000647664.

(List continued on next page.)

*Primary Examiner*—Theodore J. Criares
*Attorney, Agent, or Firm*—Oblon, Spivak, McClelland, Maier & Neustadt, P.C.

[57] ABSTRACT

Autoimmune diseases, cell adhesion inhibition and immunomodulation are treated or effected by a method, comprising, treating a patient with a therapeutically effective amount of a 4H-1-benzopyran-4-one compound represented by the following formula or a salt thereof:

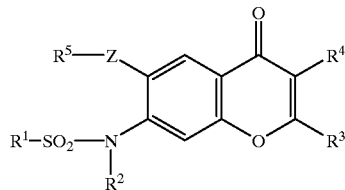

wherein $R^1$ is an unsubstituted or halogen-substituted alkyl, alkenyl or aryl group; $R^2$ is a hydrogen atom or an alkyl or acyl group; $R^3$ is a hydrogen or halogen atom or a cyano, azido, carboxyl, hydroxyl, formyl or alkoxycarbonyl group or a substituted or unsubstituted alkyl, alkoxy, phenoxy, cycloalkyl, carbamoyl, amino or phenyl group; $R^4$ is a hydrogen or halogen atom, a nitro, cyano, carboxyl, acyl, hydroxyl or alkoxycarbonyl group, or a substituted or unsubstituted alkyl, alkoxy, alkylthio, phenylthio, alkynyl, alkenyl, sulfamoyl, alkanesulfonyl, alkanesulfonyl, amidino, phenyl or heterocyclic group or a group of the formula

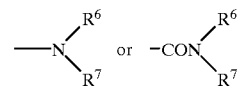

where $R^6$ is a hydrogen atom, a hydroxyl, cyano or alkoxycarbonyl group or a substituted or unsubstituted alkyl, cycloalkyl, phenyl, amino, acyl, carbamoyl, alkanesulfonyl, iminomethyl or amidino group and $R^7$ is a hydrogen atom or a substituted or unsubstituted alkyl, alkoxy, phenyl, cycloalkyl or heterocyclic group, or $R^6$ and $R^7$, when taken together with the nitrogen atom to which the two are bonded, form a 3- to 7-membered, substituted or unsubstituted heterocyclic group; $R^5$ is a substituted or unsubstituted phenyl, thienyl, furyl or pyridyl group; Z is an oxygen or sulfur atom or an imino group; and the broken line means a single or double bond.

52 Claims, No Drawings

OTHER PUBLICATIONS

Keiichi Tanaka et al, "Pharmacological Studies o n 3–Formylamino–7–methylsulfonylamino–6–phenoxy–4H–1-benzopyran–4–one (T–614), a Novel Antoinflammatory Agent. 3$^{rd}$ Communication: The Involvement of Bradykinin in Its Analgesic Actions", *J. Pharmacobio–Dyn.*, 15, pp. 641–647, 1992, XP 000647614.

Keiichi Tanaka et al, "T–614, a Novel Antirheumatic Drug, Inhibits Both the Activity and Induction of Cyclooxygenase–2 (COX–2) in Cultured Fibroblasts", *Jpn. J. Pharmacol.*, 67, pp. 305–314, 1995, XP 000647661.

Toyama Chem. Co. Ltd., WP/Derwent AN: 93–261590, XP 002028097, "Interleukin 1 and 6 prodn. inhibitors—contain preventing agents for diseases caused by production abnormality e.g. hepatitis, psoriasis etc." (1993).

IMMUNOMODULATOR, CELL ADHESION INHIBITOR, AND AGENT FOR TREATING, AND PREVENTING AUTOIMMUNE DISEASES

This application is a continuation of Ser. No. 08/530,177 filed May 6, 1996, now U.S. Pat. No. 5,922,755 and a continuation of PCT/JP94/00585 filed Apr. 7, 1994.

SPECIFICATION

The invention relates to an immunomodulating agent, a cell adhesion inhibiting agent and an agent for treating and preventing autoimmune diseases.

TECHNICAL FIELD

The present invention relates to an immunomodulating agent, a cell adhesion inhibiting agent and an agent for treating and preventing autoimmune diseases containing, as an active ingredient, a 4H-1-benzopyran-4-one derivative represented by the general formula [1] or a salt thereof:

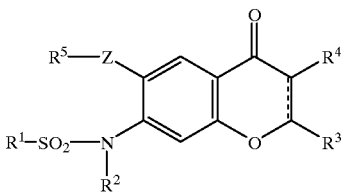

[1]

wherein $R^1$ is an unsubstituted or halogen-substituted alkyl, alkenyl or aryl group; $R^2$ is a hydrogen atom or an alkyl or acyl group; $R^3$ is a hydrogen or halogen atom or a cyano, azido, carboxyl, hydroxyl, formyl or alkoxycarbonyl group or a substituted or unsubstituted alkyl, alkoxy, phenoxy, cycloalkyl, carbamoyl, amino or phenyl group; $R^4$ is a hydrogen or halogen atom, a nitro, cyano, carboxyl, acyl, hydroxyl or alkoxycarbonyl group, or a substituted or unsubstituted alkyl, alkoxy, alkylthio, phenylthio, alkynyl, alkenyl, sulfamoyl, alkanesulfonyl, alkanesulfonyl, amidino, phenyl or heterocyclic group or a group of the formula

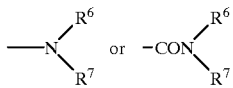

where $R^6$ is a hydrogen atom, a hydroxyl, cyano or alkoxycarbonyl group or a substituted or unsubstituted alkyl, cycloalkyl, phenyl, amino, acyl, carbamoyl, alkanesulfonyl, iminomethyl or amidino group and $R^7$ is a hydrogen atom or a substituted or unsubstituted alkyl, alkoxy, phenyl, cycloalkyl or heterocyclic group, or $R^6$ and $R^7$, when taken together with the nitrogen atom to which the two are bonded, form a 3- to 7-membered, substituted or unsubstituted heterocyclic group; $R^5$ is a substituted or unsubstituted phenyl, thienyl, furyl or pyridyl group; Z is an oxygen or sulfur atom or an imino group; and the broken line means a single or double bond.

BACKGROUND ART

The term "autoimmune disease" as used herein includes all of the diseases caused by an immune response such as an autoantibody or cell-mediated immunity to an autoantigen and the like. Examples of the diseases as described above include, for example, chronic rheumatoid arthritis, systemic lupus erythematosus, scleroderma, mixed connective tissue disease, polyarteritis nodosa, polymyositis/dermatomyositis, Sjögren's syndrome, Bechet's disease, multiple sclerosis, autoimmune diabetes, Hashimoto's disease, psoriasis, primary myxedema, pernicious anemia, myasthenia gravis, ulcerative colitis, chronic active hepatitis, autoimmune hemolytic anemia, idiopathic thrombocytopenic purpura and the like.

In general for autoimmune diseases, it has been considered that the expression of mechanism symptoms is based on hereditary factors or environmental factors. That is to say, the initiation of the autoimmune disease is, for example,a virus infection and then an immunity disorder leads to autoimmune diseases. Up to now, symptomatic treatment using non-steroidal anti-inflammatory drugs has been mainly employed in order to control the inflammatory symptoms as a method of medical treatment for the diseases noted above. However, it is presently impossible to intrinsically cure, from the standpoint of side-effects, the disease by symptomatic treatment using non-steroidal anti-inflammatory drugs even if the effect of the drug has been favorably evaluated. Under such circumstances, a treatment method to intrinsically improve an aberrant immune system and immune enhancement based on an immunomodulating action and/or a cell adhesion inhibiting action is desireable.

As a medicament having an immunomodulating action, for example, D-penicillamine and Sulfasalazine have been described in Annual reports in medicinal chemistry (Annu. Rep. Med. Chem), Vol.21, pp.201–210(1986). It is also expected that a medicament which inhibits the appearance of cell adhesion molecules on the cell surface is useful as an agent for the treatment of autoimmune diseases. See example, Arthritis and Rheumatism, Vol 36, No.2, pp.147–157(1993); and Clinical Immunology, Vol.26, No.2, pp.190–197(1994).

A derivative of 4H-1-benzopyran-4-one or a salt thereof, which is represented by the general formula [1] is known and has anti-inflammatory analgesic, antipyretic, antiarthristic and antiallergic actions, [Japanese Patent Application Kokai No.2 (1990)-49778], and has a supressive effect on the production of interleukins 1 and 6, which is useful for prevention and treatment of diseases caused by abnormal production of interleukins 1 and 6, Journal of Pharamacobio Dynamics (J. Pharmacobio-Dyn. ), Vol. 15, pp. 649–655 (1992). However, it is not known that a derivative of 4H-1-benzopyran-4-one or a salt thereof is capable of improving abnormal immunity or aberrant enhancement of cell adhesion based on an immunomodulating and/or cell adhesion inhibiting action.

So far, D-penicillamine, lobenzarit and the like have been used as immunomodulating agents or agents for autoimmune diseases. But there are few of these agents, and the effects against immunodeficiency are not sufficient. W[]hen these drugs have been used for long-term treatment, the effect of these drugs may be diminished. These drugs are never satisfactory as immunomodulating agents or agents for autoimmune diseases. Cell adhesion inhibitors have been researched for use as clinical drugs [Drug News & Perspectives, Vol.5, No.6, pp.331–337 (1992)]. Hence, the development of an agent which has a superior effect against immunodeficiency and a suppressive effect against aberrant enhancement of cell adhesion molecules, is expected to function a drug for treating and preventing autoimmune diseases.

It is an object of the present invention to provide an immunomodulating agent, a cell adhesion inhibiting agent and an agent for treating and preventing autoimmune diseases.

DISCLOSURE OF INVENTION

Under such circumstances, the present inventors have conducted extensive research to find that a 4H-1-benzopyran-4-one derivative represented by the general formula [1] or a salt thereof satisfies the desired object as described above, whereby the present invention has been completed.

The compounds in connection with the pharmaceutical agent are explained in detail below:

In the present specification, unless otherwise specified, terms have the following definitions.

The term "alkyl group" means preferably a $C_{1-8}$ alkyl group such as methyl, ethyl, n-propyl, iso-propyl, n-butyl, iso-butyl, tert-butyl, pentyl, hexyl, heptyl, octyl or the like; the term "cycloalkyl group" means preferably a $C_{3-8}$ cycloalkyl group such as cyclopropyl, cyclobutyl, cyclopentyl, cyclohexyl, cycloheptyl or the like; the term "alkenyl group" means preferably a $C_{2-8}$ alkenyl group such as vinyl, allyl, 1-propenyl, 1-butenyl or the like; the term "alkoxy group" means preferably a —O-alkyl group (alkyl group has the same meanings as defined above); the term "acyl group" means preferably a formyl group, a $C_{2-8}$ alkanoyl group such as acetyl, propionyl, butylyl or the like; alkoxyoxalyl group such as methoxalyl, ethoxalyl or the like; a $C_{3-8}$ cycloalkanecarbonyl group such as cyclohexanecarbonyl or an aroyl group such as benzoyl or the like; the term "alkoxycarbonyl group" means a —COO-alkyl group (alkyl group has the same meanings as defined above); the term "alkoxycarbonylamino group" means a —NHCOO-alkyl group (alkyl group has the same meanings as defined above); the term "halogen atom" means a fluorine atom, a chlorine atom, a bromine atom, an iodine atom or the like; the term "alkylthio group" means an —S-alkyl group (alkyl group has the same meanings as defined above); the term "alkanesulfinyl group" means preferably a $C_{1-8}$ alkanesulfonyl group such as methanesulfinyl, ethanesulfinyl or the like; the term "alkanesulfonyl group" means preferably a $C_{1-8}$ alkanesulfonyl group such as methanesulfonyl, ethanesulfonyl or the like; the term "aryl group" means preferably a phenyl, naphthyl or the like; the term "acylamino group" means a —NH-acyl group (acyl group has the same meanings as defined above); the term "alkylamino group" means a —NH-alkyl group (alkyl group has the same meanings as difined above); the term "dialkylamino group" means a —N(alkyl)$_2$ group (alkyl group has the same meanings as defined above); the term "haloalkyl group" means preferably a halo-$C_{1-8}$ alkyl group such as chloromethyl, fluoromethyl, dichloromethyl, trifluoromethyl, dichloroethyl, trichloroethyl or the like; the term "alkynyl group" means preferably a $C_{2-8}$ alkynyl group such as ethynyl, 2-propynyl or the like; the term "heterocyclic group" means preferably a 4- to 6-membered cyclic group containing at least one hetero atom selected from the group consisting of an oxygen atom, nitrogen atom and sulfur atom as the hetero atom forming the ring or a condensed cyclic group thereof, such as thienyl, furyl, pyrrolyl, oxazolyl, isoxazolyl, thiazolyl, isothiazolyl, imidazolyl, benzimidazolyl, benzthiazolyl, 1,2,3-thiadiazolyl, 1,2,4-thiadiazolyl, 1,3,4-thiadiazolyl, 1,3,4-oxadiazolyl, 1,2,3-triazolyl, 1,2,4-triazolyl, tetrazolyl, pyridyl, quinolyl, isoquinolyl, pyrimidinyl, piperadinyl, pyrazinyl, pyridazinyl, 1,2,3,4-tetrahydroquinolyl, 1,2,4-triazinyl, imidazo[1,2-b][1,2,4]triazinyl, pyrrolidinyl, morpholinyl, quinochidinyl or the like. Moreover, in the present specification, the term "lower alkyl group" means a lower alkyl group having 1 to 5 carbon atoms. In the general formula [1], when $R^6$ and $R^7$ form a 3- to 7-membered heterocyclic group with the nitrogen atom to which two are bonded, the heterocyclic group includes a nitrogen-containing heterocyclic group consisting of a 3- to 7-membered ring containing the nitrogen atom such as an azetidine-1-yl, a pyrrolidine-1-yl, a piperidine-1-yl, a pyrrole-1-yl and the like.

Additionally, the substituent of the alkyl, alkoxy, phenoxy, cycloalkyl, carbamoyl, amino and phenyl groups in $R^3$; the alkyl, alkoxy, alkylthio, phenylthio, alkynyl, alkenyl, sulfamoyl, alkanesulfinyl, alkanesulfonyl, amidino, phenyl and heterocyclic groups in $R^4$; the alkyl, cycloalkyl, phenyl, amino, acyl, carbamoyl, alkanesulfonyl, iminomethyl and amidino groups in $R^6$; the alkyl, alkoxy, phenyl, cycloalkyl and heterocyclic groups in $R^7$; the 3- to 7-membered heterocyclic groups which $R^6$ and $R^7$ form with the nitrogen atom to which the two are bonded and the phenyl, thienyl, furyl and pyridyl groups in $R^6$ may each be substituted by at least one substituent selected from the group consisting of halogen atoms, alkoxy groups, alkylthio groups, phenoxy group, carboxyl group, acyl groups, alkoxycarbonyl groups, carbamoyl group, sulfamoyl group, cyano group, alkanesulfonyl groups, hydroxyl group, mercapto group, acylamino groups, alkylamino groups, dialkylamino groups, alkyl groups, cycloalkyl groups, oxo group, nitro group, haloalkyl groups, amino group, phenyl group, alkoxycarbonylamino groups, hydroxyimino group and heterocyclic groups.

The salt of a 4H-1-benzopyran-4-one derivative of the general formula [1] includes a pharmaceutically acceptable salts, for example, salts with alkali metals such as sodium, potassium and the like; salts with alkaline earth metals such as calcium, magnesium and the like; ammonium salts; salts with organic amines such as triethylamine, pyridine and the like; salts with amino acids such as lysine, arginine, ornithine and the like; salts with mineral acids such as hydrochloric acid, hydrobromic acid, sulfuric acid and the like; salts with organic carboxylic acids such as fumaric acid, maleic acid, malic acid, citric acid and the like; and salts with sulfonic acids such as methanesulfonic acid, p-toluenesulfonic acid, naphthalenedisulfonic acid and the like.

The 4H-1-benzopyran-4-one derivertive of the general formula [1] or a salt thereof includes isomers (including geometrical isomers and optical isomers), hydrates, solvates and crystal forms.

The 4H-1-benzopyran-4-one derivative of the general formula [1] or a salt thereof can be producted by, for example, the processes described in the Japanese Patent Application Kokai No. 2 (1990)-249778.

The compounds of the present invention may be administered orally or parenterally in conventional manner in the form of capsules, powders, granules, pills, tablets, suspensions, emulsions, solutions, ointments, ampoules, syrups or suppositories. Further, the administration method, dose and number of administration times can be appropriately varied depending upon the age and symptom of a patient. Usually, the compound may be administered in several portions a day in a dose of about 5.0 to 1,000 mg per adult.

Among the 4H-1-benzopyran-4-one derivative compounds to be used as an active ingredient for the medicament, such as an immunomodulating agent, a cell adhesion inhibiting agent and an agent for treating and preventing autoimmune diseases, preferable are compounds of the general formula [1] wherein $R^1$ is a halogen-substituted or unsubstituted alkyl group; $R^2$ is a hydrogen atom; $R^3$ is a hydrogen atom or a substituted or unsubstituted alkyl group; $R^4$ is a hydrogen atom, a carboxyl group, a substituted or unsubstituted alkylthio group, a substituted or unsubstituted acylamino group or a carbamoyl group; $R^5$ is a substituted or unsubstituted phenyl group; Z is an oxygen atom or an imino group; and the broken line means a double bond. More preferable are the compound wherein $R^1$ is an alkyl group; $R^2$ is a hydrogen atom; $R^3$ is a hydrogen atom; $R^4$ is a substituted or unsubstituted acylamino group; Z is an oxygen atom; $R^8$ is a substituted or unsubstituted phenyl group; Z is an oxygen atom; and the broken line means a double bond.

Among the compounds of the present invention of a 4H-1-benzopyran-4-one derivative to be used as an active ingredient for medicament such as an immunomodulating agent, a cell adhesion inhibiting agent and an agent for treating and preventing autoimmune diseases, representative compounds thereof are as follows:

1. 3-formylamino-7-methylsulfonylamino-6-phenoxy-4H-1-benzopyran-4-one.
2. 7-methylsulfonylamino-6-phenoxy-4H-1-benzopyran-4-one.
3. 6-(2,4-difluorophenoxy)-7-methylsulfonylamino-4H-1-benzopyran-4-one.
4. 3-carbamoyl-7-methylsulfonylamino-6-phenoxy-4H-1-benzopyran-4-one.
5. 3-carbamoyl-2-methyl-7-methylsulfonylamino-6-phenoxy-4H-1-benzopyran-4-one.
6. 3-(N-formyl-N-methyl)amino-7-methylsulfonylamino-6-phenoxy-4H-1-benzopyran-4-one.
7. 3-carboxy-7-methylsulfonylamino-6-phenoxy-4H-1-benzopyran-4-one.
8. 3-methylthio-7-methylsulfonylamino-6-phenoxy-4H-1-benzopyran-4-one.
9. 6-(2,4-difluorophenylamino)-3-formylamino-7-methylsulfonylamino-4H-1-benzopyran-4-one.
10. 3-carbamoyl-6-(2,4-difluorophenylamino)-7-methylsulfonylamino-4H-1-benzopyran-4-one.
11. 2-methyl-7-methylsulfonylamino-6-phenoxy-4H-1-benzopyran-4-one
12. 6-(2-fluorophenylamino)-3-formylamino-7-methylsulfonylamino-4H-1-benzopyran-4-one.

Next, the pharmacological activities of the compounds of the present invention to be used as the agent for an immunomodulating agent, cell adhesion inhibiting agent or agent for treating and preventing autoimmune diseases are explained by experiment. The test compound numbers used in the following experiments refer to the representative compound numbers as shown above.

Experiment 1

The Effect of the Test Compounds on the Delayed-Type Hypersensitivity

Delayed-type hypersensitivity in potentiated in mice by pretreatment with cyclophosphamide was carried out in accordance with the method of P. H. Lagrange et al., Journal of Experimental Medicine, Vol.139, pp.1529–1539(1974). In brief, BALB/c male mice (8 weeks old, 6 to 8 mice per group) were pretreated with intraperitoneal injection of 75 mg/kg cyclophosphamide. Four days after the injection, 0.2 ml SRBC (sheep red blood cells) suspension ($5\times10^7$ cells/ml) was intravenously sensitized. Three days after the sensitization, delayed-type hypersensitive responses were induced with intradermally injection of 0.05 ml SRBC suspension ($8\times10^9$ cells/ml) to the left hind paw. After 24 hours, the mice were killed and both hind paws were cut off at the ankle to determine the weight of the paw. The SRBC-induced edema was measured as the difference between the left and right paw weights. The inhibitory percentage in paw edema produced by the compound treatment was expressed relative to the edema from the control mice. The test compounds were suspended in 0.5% carboxymethylcellulose (CMC) solution and were administered p.o. once a day for 5 days from 2 days prior to the sensitization. 0.5% CMC solution instead of the test compounds was administered to the control mice.

The results are shown in Table 1.

TABLE 1

| TEST COMPOUND | DOSAGE (mg/kg) | DELAYED-TYPE PAW EDEMA INHIBITIONS (%) |
|---|---|---|
| compound No. 1 | 10 | 12 |
|  | 30 | 27 |
|  | 100 | 39 |
| compound No. 2 | 100 | 17 |
| compound No. 3 | 30 | 48 |
| compound No. 4 | 100 | 41 |
| compound No. 5 | 100 | 16 |
| compound No. 6 | 100 | 17 |
| compound No. 7 | 100 | 16 |
| compound No. 8 | 100 | 21 |
| compound No. 9 | 100 | 28 |
| compound No. 10 | 100 | 20 |
| D-PENICILLAMINE | 100 | −3 |
| SULFASALAZINE | 100 | 5 |
| PREDNISOLONE | 10 | 44 |

As shown in Table 1, the test compounds cause the suppression of a delayed-type hypersensitive response in potentiative immune mice. The suppressive activity of the test compounds is equal to that of prednisolone, and more than that of D-penicillamine or sulfasalazine.

Experiment 2

Effect of the Test Compounds on the Hemolytic Plaque Forming Cell (PFC) Response $BDF_1$ male mice (6 to 7 mice per group) were intravenously injected with $2\times10^6$ or $2\times10^8$ SRBC(sh injection, the mice were killed and their spleens were excised. The number of hemolytic plaque forming cells (PFC) per spleen was determined according to the method of Cunningham et al. Immunology, Vol.14, p559 (1968) on the basis of the method by N. K. Jerne et al., Science, Vol.140, p405 (1963). The percentage change in PFC number produced by the test compounds was expressed relative to the PFC number from the control group. The test compounds were suspended in 0.5% CMC solution. The compounds were orally administered for 3 days from a day prior to injection. 0.5% CMC solution instead of the test compounds was administered to the control mice.

The results are shown in Table 2.

TABLE 2

| TREATMENT | DOSAGE (mg/kg) | PFC No./ SPLEEN[a] × 10³ | PERCENTAGE OF CONTROL GROUP |
|---|---|---|---|
| 2 × 10⁶ cells Sensitization | | | |
| control group | — | 240 ± 8 | 100 |
| compound No. 1 | 1 | 231 ± 18 | 963 |
| | 10 | 221 ± 17 | 92 |
| | 100 | 129 ± 20 | 54 |
| PREDNISOLONE | 10 | 17 ± 3 | 7 |
| 2 × 10⁶ cells Sensitization | | | |
| control group | — | 4.87 ± 0.53 | 100 |
| compound No. 1 | 1 | 7.06 ± 1.17 | 145 |
| | 10 | 7.13 ± 0.52 | 146 |
| | 100 | 5.40 ± 0.49 | 111 |
| PREDNISOLONE | 10 | 3.97 ± 0.78 | 81 |

[a]Each value is the mean ± S.E.

As shown in Table 2, the test compounds showed the obvious diminution in the PFC numbers under the optimal dose of SRBC and augmentation under the suboptimal dose. These findings indicate that the test compounds exhibit either suppression under an abnormal enhanced immune response or potentiation under a low immune response, and that the test compounds have immunomodulatory activities.

Experiment 3

Effect of the Test Compounds on Experimental Allergic Encep-Haromyelitis

Experimental allergic encepharomyelitis (EAE) is a prototype for cell-mediated autoimmune diseases, and has been widely used as an animal model of multiple sclerosis. According to the method described by Deguchi et al., Brain and Nerve, Vol.42, pp.391–397(1990), EAE was induced by using Lewis female rats (5 rats per group). In brief, rats were immunized s.c. in both hind paws with 0.1 ml emulsion, composed of a 50% guinea pig spinal cord homogenate and an equal volume of complete Freund's adjuvant. Rats were observed daily from the day of immunizaton to day 18 for clinical symptoms of EAE and the scoring system used was as follows;

0:no symptoms
1:flaccid tail
2:incomplete paralysis of hind limb
3:complete paralysis of hind limb
4:quadriplegia or death The test compound suspended in 0.5% CMC solution was orally administered once a day from the day (day 0) of immunization to day 13 and the animal was observed daily to day 18 for clinical symptoms of EAE. 0.5% CMC solution instead of the test compound was administered to the control rats. The cumulative score of the symptoms for 18 days was obtained and the inhibitory percentage in the cumulative score produced by the test compound group was expressed relative to the cumulative score from the control group.

The results are shown in Table 3.

TABLE 3

| TEST COMPOUND | DOSAGE (mg/kg) | INHIBITION (%) OF CLINICAL SCORE |
|---|---|---|
| compound No. 1 | 1 | 21 |
| | 100 | 67 |
| compound No. 3 | 30 | 86 |
| compound No. 4 | 30 | 50 |
| compound No. 6 | 30 | 66 |
| compound No. 7 | 30 | 50 |
| compound No. 8 | 30 | 17 |
| compound No. 9 | 30 | 50 |
| compound No. 10 | 30 | 42 |
| compound No. 11 | 30 | 52 |
| compound No. 12 | 30 | 67 |
| D-PENICILLAMINE | 100 | −10 |
| SULFASALAZINE | 300 | 1 |
| PREDNISOLONE | 10 | 52 |

As shown in Table 3, the test compounds cause the inhibition of the appearence and the severity of EAE. The test compounds are equal to that of prednisolone, and more than that of D-penicillamine or sulfasalazine.

Experiment 4

Effect of the Compounds on the Expression of Cell Adhesion Molecule (Very Late Antigen-4:VLA-4) in EAE Rats VLA-4 is one of the cell adhesion molecules which may be involved in the migration of lymphocytes. The effect of the compounds on the expression of VLA-4 on lymphocytes from EAE rats was examined. According to the method described in Experiment 3, rats (7 rats per group) were immunized s.c. in both hind paw with 0.1 ml emulsion, composed of a 50% guinea pig spinal cord homogenate and an equal volume of complete Freund's adjuvant. Ten days after immunization, blood was withdrawn by vena cava inferior in heparin from the rats anesthetized with ether. The leukocyte fraction was isolated from 5 ml of the blood by density gradient centrifugation. 5×10⁵ of the leukocytes were suspended in 0.5 ml of phosphate buffered saline (PBS) containing 0.1% bovine serum albumin and then reacted with 5 $\mu$l of mouse anti-rat VLA-4 antibody. After incubation at 4° C. for 1 hour, the cells were reacted with fluorescence isothiocyanate-conjugated sheep anti-mouse immunoglobulin for a further 30 min. The cells were washed with PBS and were analyzed on flow cytometry. The lymphocyte population was isolated to construct on based a forward and 90° light scatter. The results were expressed as a percentage of VLA-4 positive cell number to the lymphocyte number.

The results are as shown in Table 4.

TABLE 4

| TREATMENT | DOSAGE (mg/kg) | PERCENTAGE OF VLA-4 POSITIVE CELL (MEAN) |
|---|---|---|
| control group | — | 29.9 |
| compound No. 1 | 100 | 12.0 |

As shown in Table 4, treatment with the test compound produce a decrease in the percentage of VLA-4 positive cells as compared with the control group.

Experiment 5

Effect of the Test Compounds on the Enhanced Expression of Cell Adhesion Molecule CD11b in HL-60 (Human Promyelocytic Leukemia Cell Line) Stimulated by Phorbol Myristate Acetate (PMA)

CD11b is the α-chain of cell adhesion molucule Mac-1, which is expressed in the activation of monocytes. The effect of the test compounds on the expression of CD11b on monocytes, HL-60 cells was analyzed. In brief, $5 \times 10^5$ HL-60 cells were suspended in 2 ml of RPMI-1640 containing 10% fetal calf serum (FCS) in each well of a 12-well multiplate, and then PMA (3 mg/ml final concentration) and the test compound were added to the medium. After incubation at 37° C. for 24 hours in an atmosphere containig 5% $CO_2$, the cells were collected and was hed with PBS. $3 \times 10^3$ HL-60 cells were resuspended in 300 μl PBS (containing 1% FCS) and incubated with 5 μl of phycoerythrin-conjugated mouse anti-human CD11b antibody. After 1 hour incubation at 4° C., the cells were washed with PBS. The cells were analyzed on flow cytometry, and the results were expressed as the enhanced percentage of CD11b positive cells in the treated group relative to the PMA-untreated group.

The results are as shown in Table 5.

TABLE 5

| TEST COMPOUND | CONCENTRATION (μg/ml) | NUMBER OF MEASUREMENT | CD11b INCREASED RATE OF EXPRESSION (%) MEAN ± S.E. |
|---|---|---|---|
| control | — | 6 | 82.2 ± 4.9 |
| compound No. 1 | 10 | 6 | 49.9 ± 1.8 |

As shown in Table 5, the test compound suppresses the enhanced expression of CD11b positive cells by PMA stimulaton. Taken together with our study, the test compounds inhibit expression of and the enhanced expression of the adhesion molecules. These findings show that the compounds have the ability to inhibit cell adhesion molecules.

BEST MODE FOR CARRYING OUT THE PRESENT INVENTION

The following examples serve to illustrate and explain the pharmaceutical preparation of the present invention, but the preparation or the experiments of the present invention should not be limited thereto. In addition to the above, the compounds numbers used in the examples appearing hereinafter are in accord with each of the test compound numbers as described above.

EXAMPLE 1

In conventional manner, there is prepared the desired hard gelatin capsule containing the following ingredients.

| | |
|---|---|
| Compound 1 (test compound number 1) | 50 mg |
| Lactose | 114.5 mg |
| Cornstarch | 20 mg |
| Hydroxypropylcellulose | 2 mg |
| Light anhydrous silicic acid | 1.5 mg |
| Carboxymethylcellulose Calcium | 10 mg |
| Magnesium stearate | 2 mg |
| Total | 200 mg |

EXAMPLE 2

In conventional method, there is prepared the desired tablet containing the following ingredients.

| | |
|---|---|
| Compound 1 (test compound number 1) | 25 mg |
| Lactose | 49 mg |
| Microcrystalline cellulose | 36 mg |
| Hydroxypropylcellulose | 1 mg |
| Carboxymethylcellulose Calcium | 6.6 mg |
| Magnesium stearate | 1.2 mg |
| Talc | 1.2 mg |
| Total | 120 mg |

EXAMPLE 3

In conventional method, there is prepared the desired tablet containing the following ingredients.

| | |
|---|---|
| Compound 1 (test compound number 1) | 50 mg |
| Lactose | 74 mg |
| Microcrystalline cellulose | 55 mg |
| Hydroxypropylcellulose | 2 mg |
| Carboxymethylcellulose Calcium | 15 mg |
| Magnesium stearate | 2 mg |
| Talc | 2 mg |
| Total | 200 mg |

EXAMPLE 4

In conventional method, there is prepared the desired tablet containing the following ingredients.

| | |
|---|---|
| Compound 1 (test compound number 1) | 100 mg |
| Lactose | 49 mg |
| Microcrystalline cellulose | 55 mg |
| Hydroxypropylcellulose | 2 mg |
| Carboxymethylcellulose Calcium | 15 mg |
| Magnesium stearate | 2 mg |
| Talc | 2 mg |
| Total | 225 mg |

EXAMPLE 5

In conventional method, there is prepared the desired tablet containing the following ingredients.

| | |
|---|---|
| Compound 2 (test compound number 2) | 200 mg |
| Microcrystallinecellulose | 100 mg |
| Sodium starch glycolate | 30 mg |
| Magnesium stearate | 3 mg |
| Total | 333 mg |

INDUSTRIAL APPLICABILITY

A 4H-1-benzopyran-4-one derivative of the general formula [1] or a salt thereof, exhibits excellent effects on immunomodulation and on cell adhesion inhibition, and is further expected to have the effect of relieving autoimmune diseases at a level comparable to that of steroids. Thus, the compound of the general formula [1] is useful in the treatment and prevention of autoimmune diseases fundamentally caused by immunopathy or unusually accelerated cell adhesion, for example, in chronic rheumatoid arthritis, systemic lupus erythematosus, scleroderma, mixed connective tissue disease, polyarteritis nodosa, polymyositis/dermatomyositis, Sjögren's syndrome, Bechet's disease, multiple sclerosis, autoimmune diabetes, Hashimoto's disease, psoriasis, primary myxedema, pernicious anemia, serious adynamia, ulcerative colitis, chronic active hepatitis, autoimmune hemolytic anemia and idiopathic thrombocytopenic purpura.

What is claimed is:

1. A method of treating autoimmune diseases, comprising: treating a patient with a therapeutically effective amount of a 4H-1-benzopyran-4-one compound represented by the following formula or a salt thereof:

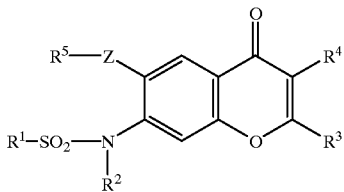

wherein $R^1$ is an unsubstituted or halogen-substituted alkyl, alkenyl or aryl group; $R^2$ is a hydrogen atom or an alkyl or acyl group; $R^3$ is a hydrogen or halogen atom or a cyano, azido, carboxyl, hydroxyl, formyl or alkoxycarbonyl group or a substituted or unsubstituted alkyl, alkoxy, phenoxy, cycloalkyl, carbamoyl, amino or phenyl group; $R^4$ is a hydrogen or halogen atom, a nitro, cyano, carboxyl, acyl, hydroxyl or alkoxycarbonyl group, or a substituted or unsubstituted alkyl, alkoxy, alkylthio, phenylthio, alkynyl, alkenyl, sulfamoyl, alkanesulfinyl, alkanesulfonyl, amidino, phenyl or heterocyclic group or a group of the formula

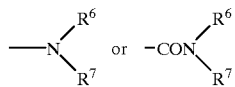

where $R^6$ is a hydrogen atom, a hydroxyl, cyano or alkoxycarbonyl group or a substituted or unsubstituted alkyl, cycloalkyl, phenyl, amino, acyl, carbamoyl, alkanesulfonyl, iminomethyl or amidino group and $R^7$ is a hydrogen atom or a substituted or unsubstituted alkyl, alkoxy, phenyl, cycloalkyl or heterocyclic group, or $R^6$ and $R^7$, when taken together with the nitrogen atom to which the two are bonded, form a 3- to 7-membered, substituted or unsubstituted heterocyclic group; $R^5$ is a substituted or unsubstituted phenyl, thienyl, furyl or pyridyl group; Z is an oxygen or sulfur atom or an imino group; and the broken line means a single or double bond.

2. The method of claim 1, wherein $R^1$ is an unsubstituted or halogen-substituted lower alkyl, lower alkenyl or aryl group; $R^2$ is a hydrogen atom or an alkyl or acyl group; $R^3$ is a hydrogen or halogen atom or a cyano, azido, carboxyl, hydroxyl, formyl or alkoxycarbonyl group or a substituted or unsubstituted alkyl, alkoxy, phenoxy, cycloalkyl, carbamoyl, amino or phenyl group; $R^4$ is a hydrogen or halogen atom, a nitro, cyano, carboxyl, acyl, hydroxyl or alkoxycarbonyl group, or a substituted or unsubstituted alkyl, alkoxy, alkylthio, phenylthio, lower alkynyl, lower alkenyl, sulfamoyl, lower alkanesulfonyl, lower alkanesulfonyl, amidino, phenyl or heterocyclic group or a group of the formula

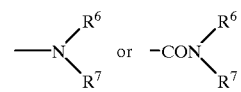

where $R^6$ is a hydrogen atom, a hydroxyl, cyano or alkoxycarbonyl group or a substituted or unsubstituted alkyl, cycloalkyl, phenyl, amino, acyl, carbamoyl, alkanesulfonyl, iminomethyl or amidino group and $R^7$ is a hydrogen atom or a substituted or unsubstituted alkyl, alkoxy, phenyl, cycloalkyl or heterocyclic group, or $R^6$ and $R^7$, when taken together with the nitrogen atom to which the two are bonded, form a 3- to 7-membered substituted or unsubstituted heterocyclic group; $R^5$ is a substituted or unsubstituted phenyl, thienyl, furyl or pyridyl group; Z is an oxygen or sulfur atom or an imino group; and the broken line means a single or double bond.

3. The method of claim 1, wherein $R^1$ is an unsubstituted or halogen-substituted alkyl group; $R^2$ is a hydrogen atom; $R^3$ is a hydrogen atom or a substituted or unsubstituted alkyl group; $R^4$ is a hydrogen atom, a carboxyl group or a substituted or unsubstituted alkylthio or acylamino group or a carbamoyl group; $R^5$ is a substituted or unsubstituted phenyl group; Z is an oxygen atom or an imino group and the broken line means a double bond.

4. The method of claim 1, wherein $R^1$ is an unsubstituted or halogen-substituted lower alkyl group; $R^2$ is a hydrogen atom; $R^3$ is a hydrogen atom or a substituted or unsubstituted alkyl group; $R^4$ is a hydrogen atom, a carboxyl group or a substituted or unsubstituted alkylthio or acylamino group or a carbamoyl group; $R^5$ is a substituted or unsubstituted phenyl group; Z is an oxygen atom or an imino group and the broken line means a double bond.

5. The method of claim 2, wherein $R^3$ is a hydrogen atom; $R^4$ is a substituted or unsubstituted acylamino group; and Z is an oxygen atom.

6. The method of claim 1, wherein said 4H-1-benzopyran-4-one compound is 3-formylamino-7-methylsulfonylamino-6-phenoxy-4H-1-benzopyran-4-one.

7. The method of claim 1, wherein said 4H-1-benzopyran-4-one compound is 7-methylsulfonylamino-6-phenoxy-4H-1-benzopyran-4-one.

8. The method of claim 1, wherein said 4H-1-benzopyran-4-one compound is 6-(2,4-difluorophenoxy)-7-methylsulfonylamino-4H-1-benzopyran-4-one.

9. The method of claim 1, wherein said 4H-1-benzopyran-4-one compound is 3-carbamoyl-7-methylsulfonylamino-6-phenoxy-4H-1-benzopyran-4-one.

10. The method of claim 1, wherein said 4H-1benzopyran-4-one compound is 3-carbamoyl-2-methyl-7-methylsulfonylamino-6-phenoxy-4H-1-benzopyran-4-one.

11. The method of claim 1, wherein said 4H-1-benzopyran-4-one compound is 3-(N-formyl-N-methyl)amino-7-methylsulfonylamino-6-phenoxy-4H-1-benzopyran-4-one.

12. The method of claim 1, wherein said 4H-1-benzopyran-4-one compound is 3-carboxy-7-methylsulfonylamino-6-phenoxy-4H-1-benzopyran-4-one.

13. The method of claim 1, wherein said 4H-1-benzopyran-4-one compound is 3-methylthio-7-methylsulfonylamino-6-phenoxy-4H-1-benzopyran-4-one.

14. The method of claim 1, wherein said 4H-1-benzopyran-4-one compound is 6-(2,4-difluorophenylamino)-3-formylamino-7-methylsulfonylamino-4H-1-benzopyran-4-one.

15. The method of claim 1, wherein said 4H-1-benzopyran-4-one compound is 3-carbamoyl-6-(2,4-difluorophenylamino)-7-methylsulfonylamino-4H-1-benzopyran-4-1-one.

16. The method of claim 1, wherein said 4H-1-benzopyran-4-one compound is 2-methyl-7-methylsulfonylamino-6-phenoxy-4H-1-benzopyran-4-one.

17. The method of claim 1, wherein said 4H-1-benzopyran-4-one compound is 6-(2-fluorophenylamino)-3-formylamino-7-methylsulfonylamino-4H-1-benzopyran-4-one.

18. The method of claim 1, wherein said autoimmune disease is chronic rheumatoid arthritis, systemic lupus erythematosus, scleroderma, mixed connective tissue disease, polyarteritis nodosa, polymyositis/dermatomyositis, Sjögren's syndrome, Bechet's disease, multiple sclerosis, autoimmune diabetes, Hashimoto's disease, psoriasis, primary myxedema, pernicious anemia, myasthenia gravis, ulcerative colitis, chronic active hepatitis, autoimmune hemolytic anemia, or idiopathic thrombocytopenic purpura.

19. A method of inhibiting cell adhesion, comprising:
administering to a patient a cell adhesion inhibiting amount of a 4H-1-benzopyran-4-one compound represented by the following formula or a salt thereof:

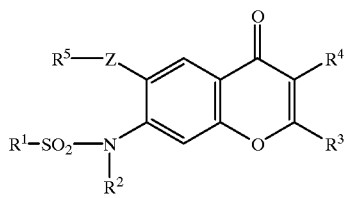

wherein $R^1$ is an unsubstituted or halogen-substituted alkyl, alkenyl or aryl group; $R^2$ is a hydrogen atom or an alkyl or acyl group; $R^3$ is a hydrogen or halogen atom or a cyano, azido, carboxyl, hydroxyl, formyl or alkoxycarbonyl group or a substituted or unsubstituted alkyl, alkoxy, phenoxy, cycloalkyl, carbamoyl, amino or phenyl group; $R^4$ is a hydrogen or halogen atom, a nitro, cyano, carboxyl, acyl, hydroxyl or alkoxycarbonyl group, or a substituted or unsubstituted alkyl, alkoxy, alkylthio, phenylthio, alkynyl, alkenyl, sulfamoyl, alkanesulfinyl, alkanesulfonyl, amidino, phenyl or heterocyclic group or a group of the formula:

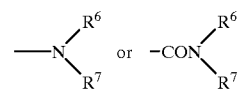

where $R^6$ is a hydrogen atom, a hydroxyl, cyano or alkoxycarbonyl group or a substituted or unsubstituted alkyl, cycloalkyl, phenyl, amino, acyl, carbamoyl, alkanesulfonyl, iminomethyl or amidino group and $^7$ is a hydrogen atom or a substituted or unsubstituted alkyl, alkoxy, phenyl, cycloalkyl or heterocyclic group, or $R^6$ and $R^7$, when taken together with the nitrogen atom to which the two are bonded, form a 3- to 7-membered, substituted or unsubstituted heterocyclic group; $R^5$ is a substituted or unsubstituted phenyl, thienyl, furyl or pyridyl group; Z is an oxygen or sulfur atom or an imino group; and the broken line means a single or double bond.

20. The method of claim 19, wherein $R^1$ is an unsubstituted or halogen-substituted lower alkyl, lower alkenyl or aryl group; $R^2$ is a hydrogen atom or an alkyl or acyl group; $R^3$ is a hydrogen or halogen atom or a cyano, azido, carboxyl, hydroxyl, formyl or alkoxycarbonyl group or a substituted or unsubstituted alkyl, alkoxy, phenoxy, cycloalkyl, carbamoyl, amino or phenyl group; $R^4$ is a hydrogen or halogen atom, a nitro, cyano, carboxyl, acyl, hydroxyl or alkoxycarbonyl group, or a substituted or unsubstituted alkyl, alkoxy, alkylthio, phenylthio, lower alkynyl, lower alkenyl, sulfamoyl, lower alkanesulfonyl, lower alkanesulfonyl, amidino, phenyl or heterocyclic group or a group of the formula

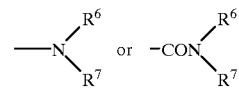

where $R^6$ is a hydrogen atom, a hydroxyl, cyano or alkoxycarbonyl group or a substituted or unsubstituted alkyl, cycloalkyl, phenyl, amino, acyl, carbamoyl, alkanesulfonyl, iminomethyl or amidino group and $R^7$ is a hydrogen atom or a substituted or unsubstituted alkyl, alkoxy, phenyl, cycloalkyl or heterocyclic group, or $R^6$ and $R^7$, when taken together with the nitrogen atom to which the two are bonded, form a 3- to 7-membered substituted or unsubstituted heterocyclic group; $R^5$ is a substituted or unsubstituted phenyl, thienyl, furyl or pyridyl group; Z is an oxygen or sulfur atom or an imino group; and the broken line means a single or double bond.

21. The method of claim 19, wherein $R^1$ is an unsubstituted or halogen-substituted alkyl group; $R^2$ is a hydrogen atom; $R^3$ is a hydrogen atom or a substituted or unsubstituted alkyl group; $R^4$ is a hydrogen atom, a carboxyl group or a substituted or unsubstituted alkylthio or acylamino group or a carbamoyl group; $R^5$ is a substituted or unsubstituted phenyl group; Z is an oxygen atom or an imino group and the broken line means a double bond.

22. The method of claim 18, wherein $R^1$ is an unsubstituted or halogen-substituted lower alkyl group; $R^2$ is a hydrogen atom; $R^3$ is a hydrogen atom or a substituted or unsubstituted alkyl group; $R^4$ is a hydrogen atom, a carboxyl group or a substituted or unsubstituted alkylthio or acylamino group or a carbamoyl group; $R^5$ is a substituted or unsubstituted phenyl group; Z is an oxygen atom or an imino group and the broken line means a double bond.

23. The method of claim 21, wherein $R^3$ is a hydrogen atom; $R^4$ is a substituted or unsubstituted acylamino group; and Z is an oxygen atom.

24. The method of claim 19, wherein said 4H-1-benzopyran-4-one compound is 3-formylamino-7-methylsulfonylamino-6-phenoxy-4H-1-benzopyran-4-one.

25. The method of claim 19, wherein said 4H-1benzopyran-4-one compound is 7-methylsulfonylamino-6-phenoxy-4H-1-benzopyran-4-one.

26. The method of claim 19, wherein said 4H-1-benzopyran-4-one compound is 6-(2,4-difluorophenoxy)-7-methylsulfonylamino-4H-1-benzopyran-4-one.

27. The method of claim 19, wherein said 4H-1-benzopyran-4-one compound is 3-carbamoyl-7-methylsulfonylamino-6-phenoxy-4H-1-benzopyran-4-one.

28. The method of claim 19, wherein said 4H-1-benzopyran-4-one compound is 3-carbamoyl-2-methyl-7-methylsulfonylamino-6-phenoxy-4H-1-benzopyran-4-one.

29. The method of claim 19, wherein said 4H-1-benzopyran-4-one compound is 3-(N-formyl-N-methyl)amino-7-methylsulfonylamino-6-phenoxy-4H-1-benzopyran-4-one.

30. The method of claim 19, wherein said 4H-1-benzopyran-4-one compound is 3-carboxy-7-methylsulfonylamino-6-phenoxy-4H-1-benzopyran-4-one.

31. The method of claim 19, wherein said 4H-1-benzopyran-4-one compound is 3-methylthio-7-methylsulfonylamino-6-phenoxy-4H-1-benzopyran-4-one.

32. The method of claim 19, wherein said 4H-1-benzopyran-4-one compound is 6-(2,4-difluorophenylamino)-3-formylamino-7-methylsulfonylamino-4H-1-benzopyran-4-one.

33. The method of claim 19, wherein said 4H-1-benzopyran-4-one compound is 3-carbamoyl-6-(2,4-difluorophenylamino)-7-methylsulfonylamino-4H-1-benzopyran-4-one.

34. The method of claim 19, wherein said 4H-1-benzopyran-4-one compound is 2-methyl-7-methylsulfonylamino-6-phenoxy-4H-1-benzopyran-4-one.

35. The method of claim 19, wherein said 4H-1-benzopyran-4-one compound is 6-(2-fluorophenylamino)-3-formylamino-7-methylsulfonylamino-4H-1-benzopyran-4-one.

36. A method of immunomodulation, comprising:
administering to a patient a cell adhesion inhibiting amount of a 4H-1-benzopyran-4-one compound represented by the following formula or a salt thereof:

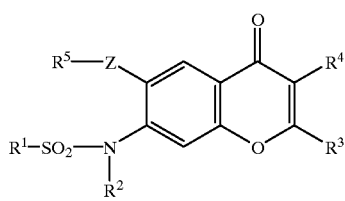

wherein $R^1$ is an unsubstituted or halogen-substituted alkyl, alkenyl or aryl group; $R^2$ is a hydrogen atom or an alkyl or acyl group; $R^3$ is a hydrogen or halogen atom or a cyano, azido, carboxyl, hydroxyl, formyl or alkoxycarbonyl group or a substituted or unsubstituted alkyl, alkoxy, phenoxy, cycloalkyl, carbamoyl, amino or phenyl group; $R^4$ is a hydrogen or halogen atom, a nitro, cyano, carboxyl, acyl, hydroxyl or alkoxycarbonyl group, or a substituted or unsubstituted alkyl, alkoxy, alkylthio, phenylthio, alkynyl, alkenyl, sulfamoyl, alkanesulfinyl, alkanesulfonyl, amidino, phenyl or heterocyclic group or a group of the formula

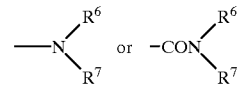

where $R^6$ is a hydrogen atom, a hydroxyl, cyano or alkoxycarbonyl group or a substituted or unsubstituted alkyl, cycloalkyl, phenyl, amino, acyl, carbamoyl, alkanesulfonyl, iminomethyl or amidino group and $R^7$ is a hydrogen atom or a substituted or unsubstituted alkyl, alkoxy, phenyl, cycloalkyl or heterocyclic group, or $R^6$ and $R^7$, when taken together with the nitrogen atom to which the two are bonded, form a 3- to 7-membered, substituted or unsubstituted heterocyclic group; $R^5$ is a substituted or unsubstituted phenyl, thienyl, furyl or pyridyl group; Z is an oxygen or sulfur atom or an imino group; and the broken line means a single or double bond.

37. The method of claim 36, wherein $R^1$ is an unsubstituted or halogen-substituted lower alkyl, lower alkenyl or aryl group; $R^2$ is a hydrogen atom or an alkyl or acyl group; $R^3$ is a hydrogen or halogen atom or a cyano, azido, carboxyl, hydroxyl, formyl or alkoxycarbonyl group or a substituted or unsubstituted alkyl, alkoxy, phenoxy, cycloalkyl, carbamoyl, amino or phenyl group; $R^4$ is a hydrogen or halogen atom, a nitro, cyano, carboxyl, acyl, hydroxyl or alkoxycarbonyl group, or a substituted or unsubstituted alkyl, alkoxy, alkylthio, phenylthio, lower alkynyl, lower alkenyl, sulfamoyl, lower alkanesulfinyl, lower alkanesulfonyl, amidino, phenyl or heterocyclic group or a group of the formula

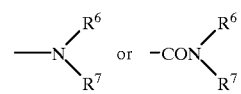

where $R^6$ is a hydrogen atom, a hydroxyl, cyano or alkoxycarbonyl group or a substituted or unsubstituted alkyl, cycloalkyl, phenyl, amino, acyl, carbamoyl, alkanesulfonyl, iminomethyl or amidino group and $R^7$ is a hydrogen atom or a substituted or unsubstituted alkyl, alkoxy, phenyl, cycloalkyl or heterocyclic group, or $R^6$ and $R^7$, when taken together with the nitrogen atom to which the two are bonded, form a 3- to 7-membered substituted or unsubstituted heterocyclic group; $R^5$ is a substituted or unsubstituted phenyl, thienyl, furyl or pyridyl group; Z is an oxygen or sulfur atom or an imino group; and the broken line means a single or double bond.

38. The method of claim 36, wherein $R^3$ is an unsubstituted or halogen-substituted alkyl group; $R^2$ is a hydrogen atom; $R^3$ is a hydrogen atom or a substituted or unsubstituted alkyl group; $R^4$ is a hydrogen atom, a carboxyl group or a substituted or unsubstituted alkylthio or acylamino group or a carbamoyl group; $R^5$ is a substituted or unsubstituted phenyl group; Z is an oxygen atom or an imino group and the broken line means a double bond.

39. The method of claim 36, wherein $R^1$ is an unsubstituted or halogen-substituted lower alkyl group; $R^2$ is a hydrogen atom; $R^3$ is a hydrogen atom or a substituted or unsubstituted alkyl group; $R^4$ is a hydrogen atom, a carboxyl group or a substituted or unsubstituted alkylthio or acylamino group or a carbamoyl group; $R^5$ is a substituted or unsubstituted phenyl group; Z is an oxygen atom or an imino group and the broken line means a double bond.

40. The method of claim 38, wherein $R^3$ is a hydrogen atom; $R^4$ is a substituted or unsubstituted acylamino group; and Z is an oxygen atom.

41. The method of claim 36, wherein said 4H-1-benzopyran-4-one compound is 3-formylamino-7-methylsulfonylamino-6-phenoxy-4H-1-benzopyran-4-one.

42. The method of claim 36, wherein said 4H-1-benzopyran-4-one compound is 7-methylsulfonylamino-6-phenoxy-4H-1-benzopyran-4-one.

43. The method of claim 36, wherein said 4H-1-benzopyran-4-one compound is 6-(2,4-difluorophenoxy)-7-methylsulfonylamino-4H-1-benzopyran-4-one.

44. The method of claim 36, wherein said 4H-1-benzopyran-4-one compound is 3-carbamoyl-7-methylsulfonylamino-6-phenoxy-4H-1-benzopyran-4-one.

45. The method of claim 36, wherein said 4H-1-benzopyran-4-one compound is 3-carbamoyl-2-methyl-7-methylsulfonylamino-6-phenoxy-4H-1-benzopyran-4-one.

46. The method of claim 36, wherein said 4H-1-benzopyran-4-one compound is 3-formyl-N-methyl)amino-7-methylsulfonylamino-6-phenoxy-4H-1-benzopyran-4-one.

47. The method of claim 36, wherein said 4H-1-benzopyran-4-one compound is 3-carboxy-7-methylsulfonylamino-6-phenoxy-4H-1-benzopyran-4-one.

48. The method of claim 36, wherein said 4H-1-benzopyran-4-one compound is 3-methylthio-7-methylsulfonylamino-6-phenoxy-4H-1-benzopyran-4-one.

49. The method of claim 36, wherein said 4H-1-benzopyran-4-one compound is 6-(2,4-difluorophenylamino)-3-formylamino-7-methylsulfonylamino-4H-1-benzopyran-4-one.

50. The method of claim 36, wherein said 4H-1-benzopyran-4-one compound is 3-carbamoyl-6-(2,4-difluorophenylamino)-7-methylsulfonylamino-4H-1-benzopyran-4-one.

51. The method of claim 36, wherein said 4H-1-benzopyran-4-one compound is 2-methyl-7-methylsulfonylamino-6-phenoxy-4H-1-benzopyran-4-one.

52. The method of claim 36, wherein said 4H-1-benzopyran-4-one compound is 6-(2-fluorophenylamino)-3-formylamino-7-methylsulfonylamino-4H-1-benzopyran-4-one.

* * * * *